United States Patent
Sabsabi et al.

(10) Patent No.: US 6,700,660 B2
(45) Date of Patent: *Mar. 2, 2004

(54) METHOD AND APPARATUS FOR IN-PROCESS LIQUID ANALYSIS BY LASER INDUCED PLASMA SPECTROSCOPY

(75) Inventors: Mohamad Sabsabi, Boucherville (CA); Rene Heon, Boucherville (CA); John M. Lucas, Outremont (CA)

(73) Assignees: Noranda Inc., Toronto (CA); National Research Council of Canada, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/071,529

(22) Filed: Feb. 8, 2002

(65) Prior Publication Data

US 2002/0159059 A1 Oct. 31, 2002

Related U.S. Application Data

(63) Continuation-in-part of application No. 09/778,723, filed on Feb. 8, 2001.

(51) Int. Cl.[7] .............................. G01J 3/30; G01N 21/01
(52) U.S. Cl. .................. 356/318; 356/317; 250/432 R; 250/573
(58) Field of Search ................................ 356/318, 311, 356/313, 317, 51, 36; 250/428, 430, 432 R, 435, 438, 573, 576

(56) References Cited

U.S. PATENT DOCUMENTS

| | | | | |
|---|---|---|---|---|
| 4,688,935 A | * | 8/1987 | Barnes et al. ................. | 356/36 |
| 4,730,925 A | * | 3/1988 | Chiba et al. ................. | 356/311 |
| 4,925,307 A | | 5/1990 | Cremers et al. ............ | 356/318 |
| 4,986,658 A | | 1/1991 | Kim .......................... | 356/318 |
| 5,379,103 A | | 1/1995 | Zigler ........................ | 356/73 |
| 5,400,137 A | * | 3/1995 | Winslow et al. ............ | 356/318 |
| 5,751,416 A | | 5/1998 | Singh et al. ................ | 356/311 |
| 6,008,897 A | * | 12/1999 | Sabsabi et al. ............. | 356/318 |
| 2002/0149768 A1 | * | 10/2002 | Sabsabi et al. ............. | 356/318 |

OTHER PUBLICATIONS

Wachter and Cremers, Determination of uranium in solution using laser–induced breakdown spectroscopy, Applied Spectroscopy, Vol 41(6), 1042–1048, 1987.

Arca et al, Trace element analysis in water by the laser–induced breakdown spectroscopy technique, Applied Spectroscopy, Vol 51(8), 1102–1105, 1997.

Berman et al, Laser–induced breakdown spectroscopy of liquids: aqueous solutions of nickel and chlorinated hydrocarbons, Applied Spectroscopy, Vol 52(3), 438–443, 1998.

(List continued on next page.)

*Primary Examiner*—Thong Nguyen
*Assistant Examiner*—Arnel C. Lavarias
(74) *Attorney, Agent, or Firm*—Holland & Bonzagni, P.C.; Mary R. Bonzagni, Esq.

(57) ABSTRACT

A method and apparatus for spectrochemical analysis of liquids, including molten materials, using laser-induced plasma spectroscopy. The apparatus preferably comprises a high power pulsed laser focused on the surface of a liquid stream flowing in a measurement cell, and an optical spectrometer-detector assembly, which receives, detects and analyzes the radiation emitted by the high temperature plasma thereby excited. The measurement cell, and optional pump, establish a steady flow of liquid, thereby permitting the laser to repeatedly sample a fresh unperturbed surface, representative of the liquid volume, while also ensuring that bubbles and waves formed in the liquid are removed from the focal volume. Gas (usually air) blown above the liquid prevents aerosols and matter ejected from the sample responsive to the incident energy from interacting with subsequent laser pulses, and from accumulating on the optics.

38 Claims, 4 Drawing Sheets

OTHER PUBLICATIONS

Ng et al, Spectrochemical analysis of liquids using laser-induced plasma emissions: effects of laser wavelength on plasma properties, Applied Spectroscopy, Vol 51(7), 976–983, 1997.

Ho et al, Spectrochemical analysis of liquids using laser-induced plasma emissions: effect of laser wavelength, Applied Spectroscopy, Vol 51(1), 87–91, 1997.

Winefordener et al, Laser-induced plasma atomic emission spectrometry in liquid aerosols, Analytica Chimica Acta, Vol 269(1), 123–128, 1992.

* cited by examiner

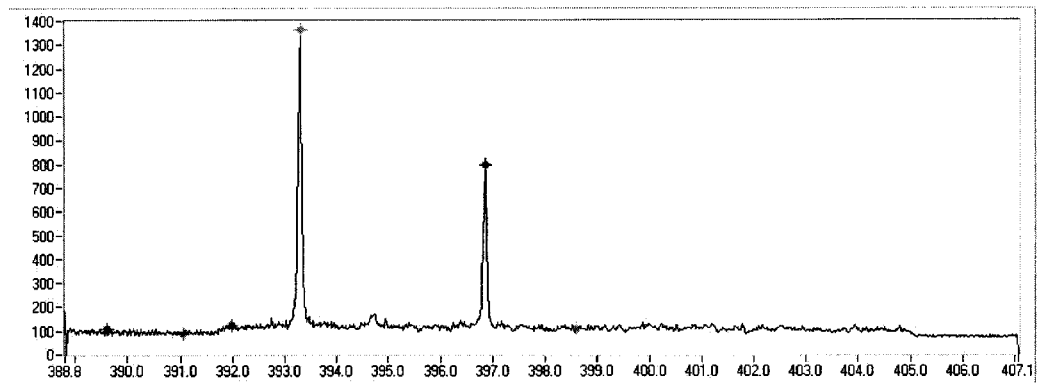
Figure 4: A spectrum obtained by focusing a YAG laser beam on the surface of water showing the calcium lines at 393.3 and 396.8 nm. The laser energy was 200 mJ.
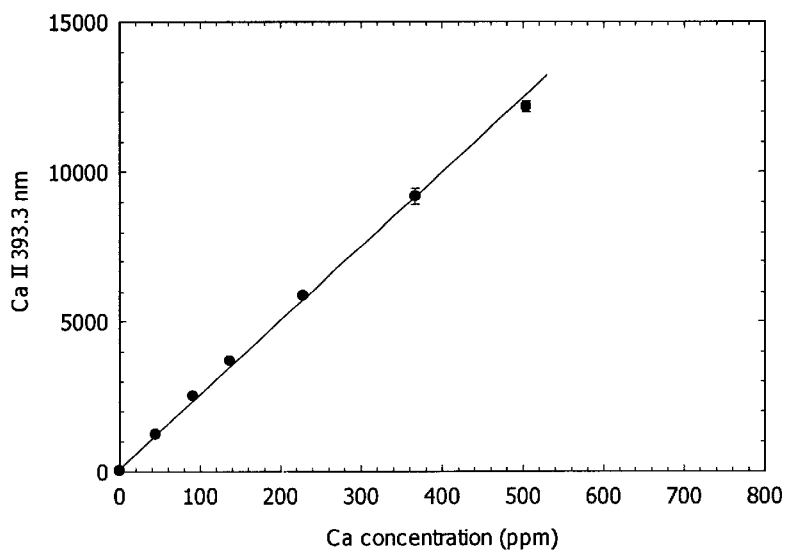
Figure 5 : Calibration curve of calcium in water

METHOD AND APPARATUS FOR IN-PROCESS LIQUID ANALYSIS BY LASER INDUCED PLASMA SPECTROSCOPY

RELATED APPLICATION

This application is a continuation-in-part of U.S. patent application Ser. No. 09/778,723, filed Feb. 8, 2001.

BACKGROUND OF THE INVENTION

1. Field of the Invention

This invention relates to an apparatus and methods for use in laser induced breakdown spectroscopy (LIBS), and for the rapid analysis of liquids including molten metals. In particular, the invention is directed to an apparatus and methods for use with LIBS system that can be applied to the real time analysis of a flowing liquid, and overcomes accuracy problems that are associated with LIBS induced aerosols including the accumulation of droplets on the laser optics, and prevents errors associated with analysis of surfaces which are not representative of the bulk as a result of surface contamination or segregation.

2. Related Art

Due to the absence of suitable on-line liquid analysis technology, there are many instances where industrial processes must be monitored by periodic liquid sampling followed by time consuming laboratory procedures, such as liquid or gas chromatography, graphite furnace atomic absorption spectroscopy, or inductively coupled plasma optical emission spectrometry. Faster in-situ methods such as spark-discharge optical spectrometry are only applicable to electrically conductive materials, while X-ray backscattering probes are limited in sensitivity.

Laser induced breakdown spectroscopy can provide rapid, in-situ compositional analysis of a variety of materials in hostile environments, and at a distance. This method includes focusing a high power pulsed laser on the material, thereby vaporizing and ionizing a small volume of the material to produce a plasma having an elemental composition that is representative of the material. The optical emission of the plasma is analyzed with an optical spectrometer to obtain its atomic composition.

A method for analyzing elements present in a sample using LIBS is known in the art. For example, a list of patents that are related can be found in U.S. Pat. No. 5,751,416, which is incorporated herein by reference. Furthermore this method has been applied to a variety of materials and industrial environments. However, the analysis of liquid by LIBS presents some challenge and suffers from problems associated with splashing, aerosols, bubbling inside the liquid, and difficulties of obtaining reproducible flowing liquid necessary for real time monitoring, as exemplified in the following documents that are related to the analysis of liquids or molten metals.

U.S. Pat. No. 4,986,658, incorporated herein by reference, describes a probe for performing molten metal analysis by laser induced plasma spectroscopy. The probe contains a high-power laser that produces a pulse that has a triangular pulse waveshape. When the probe head is immersed in molten metal, the pulsed laser beam vaporizes a portion of the molten metal to produce plasma having an elemental composition that is representative of the molten metal composition. Within the probe there is provided a pair of spectrographs, with each having a diffraction grating coupled to a gated intensified photodiode array. The spectroscopic atomic emission of the plasma is detected and analyzed for two separate time windows during the life of the plasma by using two spectrometers in parallel. The spectra obtained during either the first or the second time window, or a combination of both, can be used to infer the atomic composition of the molten metal. In this configuration for obtaining an elemental composition that is representative of the liquid, the probe head must be immersed in the liquid or the molten metal. However, the immersed probe system is not easy to use and is not suitable for use with most molten metals or melts glass. Furthermore the probe samples a stationary surface and not flowing liquid, and does not provide any solutions for the problems associated with the present invention.

U.S. Pat. No. 5,379,103, incorporated herein by reference, describes a mobile laboratory for in-situ detection of organic and heavy metal pollutants in ground water. Pulsed laser energy is delivered by fiber optics to create a laser spark on a remotely located analysis sample. The system operates in two modes, one is based on laser induced plasma spectroscopy, and the other on laser induced fluorescence. In the first operational mode, the laser beam emerging from the fiber optics is focused on the sample by a lens to generate plasma. The emitted spectrum is analyzed and used to detect heavy metals. In the second mode an unfocused ultraviolet laser beam from the fiber optics irradiates the sample, thereby exciting fluorescence from organic molecules with an aromatic structure. The emitted fluorescence is transmitted via fiber optics for further analysis. The measured spectral and temporal characteristics of the emitted fluorescence can then be compared with predetermined characteristics to identify the organic substances in the analysis sample. Again, in this patent laser pulses are used to analyze on-site pollutants in stationary ground water. This approach does not provide any arrangement related to the real time analysis of a liquid stream or proposes solutions to problems associated with the present invention.

Two temporally close sparks induced by two collinear lasers are used in U.S. Pat. No. 4,925,307, incorporated herein by reference, for the spectrochemical analysis of liquids. The laser light is not significantly absorbed by the sample so that the sparks occur in the volume inside the liquid. The spark produced by the first laser pulse produces a bubble in the liquid that stays in the gaseous state for hundreds of microseconds after the first spark has decayed, so that the second laser pulse, fired typically 18 microseconds after the first pulse, will produce a second spark within the gaseous bubble. The emission spectrum of the second spark, detected by a spectrometer oriented at 90 degrees from the laser beam axis, is thus much more intense and exhibits reduced line widths compared to the first spark, so that an increased detectability of the atomic species is obtained by sampling the bubble with the second laser spark. This approach can not be used for molten metals, opaque liquids or for real time measurement, as it is only suitable for off-line analysis of relatively transparent liquids.

As mentioned above, the use of laser induced plasma spectroscopy for analysis of liquids is known. In particular, three approaches have been described. The first approach, as used by Wachter and Cremers (Applied Spectroscopy, Vol 41(6), 1042–1048, 1987), Arca et al (Applied Spectroscopy, Vol 51(8), 1102–1105, 1997) and Berman et al (Applied Spectroscopy, Vol 52(3), 438–443, 1998), consists of focusing laser pulses onto the surface of a stationary liquid body under laboratory conditions. This approach is not useful and can not be applied for on-line measurement.

The second approach, as described by Ng et al (Applied Spectroscopy, Vol 51(7), 976–983, 1997) and Ho et al (Applied Spectroscopy, Vol 51(1), 87–91, 1997), is devoted to the analysis of liquids, which are ejected through narrow tubing to form a vertical jet. The jet is intercepted by an ablation laser about 12 mm down-stream. No mention is made of the analysis of a controlled liquid laminar flow.

The last approach, as adopted by Winefordner et al (Analytica Chimica Acta, Vol 269(1), 123–128, 1992), concerns the analysis of liquid aerosol. The liquid aerosol was generated with a commonly used Inductively Coupled Plasma-type glass concentric nebulizer assembly, and carried by the nebulization argon flow (0.51 min−1) through a small tube (1 mm diameter) into a laser induced plasma sustained in ambient laboratory air. This approach is not adequate for on-line measurement.

SUMMARY OF THE INVENTION

Briefly, the technique of the present invention is to monitor various elements in liquids, including molten metal, during normal processing operations, preferably while the liquid is flowing, as opposed to removing a sample from the liquid stream for laboratory analysis. Direct monitoring of the flowing liquid provides many advantages over discrete sampling, including the ability to adjust the process being monitored in real time based on the results of the analysis. However, the inventors have found that frequent cleaning of the optical component (focusing lens or window) may be required due to the absorption of laser and emitted light by accumulated matter that was ejected and splashed from the liquid sample in response to the incident laser pulses. Moreover, vaporization of the liquid sample during the detection and analysis process creates miniature shock waves that create aerosols in the volume above the liquid surface. As a result, the overall efficiency of the direct monitoring process suffers due to the necessity of preventing aerosols. Furthermore, it appears that laser pulses induce waves on the surface of the liquid and may induce bubbles inside some liquids that are transparent at the laser wavelength. These bubbles may reach the surface being analyzed and change the characteristics of the laser-induced plasma, thereby affecting measurement reproducibility. The reflected waves by the wall of the cell induce a movement of the surface being analyzed and affect the characteristic of the laser-induced plasma, thereby the accuracy of the measurement. Also, for liquid containing several phases the surface is not necessarily representative of the bulk, as a result, the LIBS analysis is not useful since it does not reflect the real value of the bulk.

In view of the above, the object of the present invention is to provide a method and apparatus which permits the reliable analysis of a reproducible steady controlled or laminar flow of liquid by focusing laser pulses on the surface of that liquid. Also, the invention provides a means for direct monitoring of a liquid stream with a LIBS system, while overcoming the problems associated with aerosols, debris, or droplets, on the focusing lens, thereby achieving efficient continuous LIBS analysis. The present invention both enables the laser to repeatedly sample a fresh surface representative of the volume, and largely prevents aerosols and matter ejected from the sample responsive to the incident energy from accumulating on the optics and absorbing the laser light. Furthermore, circulation of the liquid flow removes bubbles from the focal volume, and thereby prevents them from reaching the surface sampled by the laser pulse where they would interfere with measurements. Moreover, the mixer in the cell ensures a rapid uniformity of the liquid, thereby, homogeneity of that liquid is obtained which enables sampling a surface representative of the volume. Also, the weir in the cell prevents the reflection of the waves and ensures a stable surface to be sampled by the laser pulses.

Accordingly, one object of this invention is to provide an improved method and apparatus for in-situ transient spectroscopic analysis of liquids including molten metal.

A further object of this invention is to provide an apparatus that facilitates reliable real time LIBS analysis by establishing a steady flow of liquid thereby enabling the laser to sample a fresh surface, and preventing bubbles formed in the liquid from reaching the sampled surface by moving them away from the focal volume.

It is a further object of some aspects of the present invention to provide means for preventing aerosols and matter ejected from the sample responsive to the incident energy from accumulating on the optic and absorbing both the laser beam and plasma radiation entering the spectrometer optics.

It is still a further object of the present invention to provide an improved optical assembly for use in a variety of industrial environments.

According to one aspect of the present invention an apparatus is provided for the optical analysis of the concentrations of one or more elements in a liquid, by laser-induced plasma spectroscopic analysis. The apparatus comprises a means for emitting and focusing laser pulses on a surface of the liquid to generate a plasma that emits optical radiation that contains elemental radiation that is derived from separate compositional elements of the liquid; a detector; an air removal exhaust or blower to substantially prevent drops, which are ejected from the liquid in response to the incident energy, from accumulating on an optical window of said optical system; and a cell assembly, which establishes a substantially steady flow of the liquid to be analyzed, including a controller to control the liquid surface level and speed of flow, and a mixer to ensure that the surface is representative of the bulk.

According to other aspects of the present invention the probe comprises a configuration where the laser beam for sampling and the light collection measuring the radiation spectrum are substantially collinear, including the specific line emissions that are representative of selected elements present in the liquid; and data processing means for determining the concentration of the selected elements by comparison with formerly established calibration curves obtained by using standard (predetermined), precalibrated samples with different elemental concentrations independently measured by established laboratory techniques.

According to other aspects of the present invention the detector comprises a photodiode array, CCD camera, or photomultipliers individually positioned to detect both emissions from elements present in the liquid and background radiation.

According to another aspect of the present invention the means for emitting and focusing laser pulses uses multiple laser pulses for creating and exciting plasma from the liquid.

According to another aspect of the present invention the apparatus further comprises fiber optics means to convey radiation emitted by the plasma to the spectrometer.

According to another aspect of the present invention the cell assembly of the apparatus is connected to a pump that allows for circulation of the liquid in a closed loop.

According to another aspect of the present invention there is a method for optically analyzing the concentrations of one or more elements in a liquid, by laser-induced plasma spectroscopic analysis, comprising the steps of emitting and focusing laser pulses on a surface of the liquid to generate a plasma that emits optical radiation that contains elemental radiation that is derived from separate compositional elements of the liquid; detecting the optical radiation; removing or blowing air to substantially prevent drops, which are ejected from the liquid in response to the incident energy, from accumulating on an optical window of said optical system; and establishing a substantially steady flow of the liquid to be analyzed by using a controller to control the liquid surface level and speed of flow.

According to another aspect of the present invention the detecting step includes sampling and measuring the radiation spectrum, including the specific line emissions that are representative of selected elements present in the liquid using a collinear configuration and processing the data to determine the concentration of the selected elements by comparing them with formerly established calibration curves that were obtained by recording the signal levels corresponding to samples with different elemental concentrations independently measured by established laboratory techniques.

According to other aspects of the present invention the detecting step includes using a photodiode array, CCD camera, or photomultipliers individually positioned to detect both emissions from elements present in the liquid and background radiation.

According to another aspect of the present invention the emitting and focusing laser pulse step uses multiple laser pulses (simultaneous or separated by some delays) for creating and exciting plasma from the liquid.

According to another aspect of the present invention the method further comprises the step of conveying radiation emitted by the plasma to the spectrometer in said detecting step using fiber optics.

According to yet another aspect of the present invention the method further comprises the step of circulating the liquid in a closed loop by using a pump.

BRIEF DESCRIPTION OF THE DRAWINGS

These and other objects, features and advantages of the present invention will become apparent from a consideration of the following detailed description of the invention in conjunction with the drawing figures in which:

FIG. 4 shows a spectrum obtained with a Nd:YAG Q-switched laser focused on the surface of tap water in the cell showing the calcium lines at 393.3 and 396.8 nm. The laser energy was 200 mJ.

FIG. 5 shows the calibration curve for calcium in water.

DETAILED DESCRIPTION OF THE PREFERRED EMBODIMENTS

Figure 1:
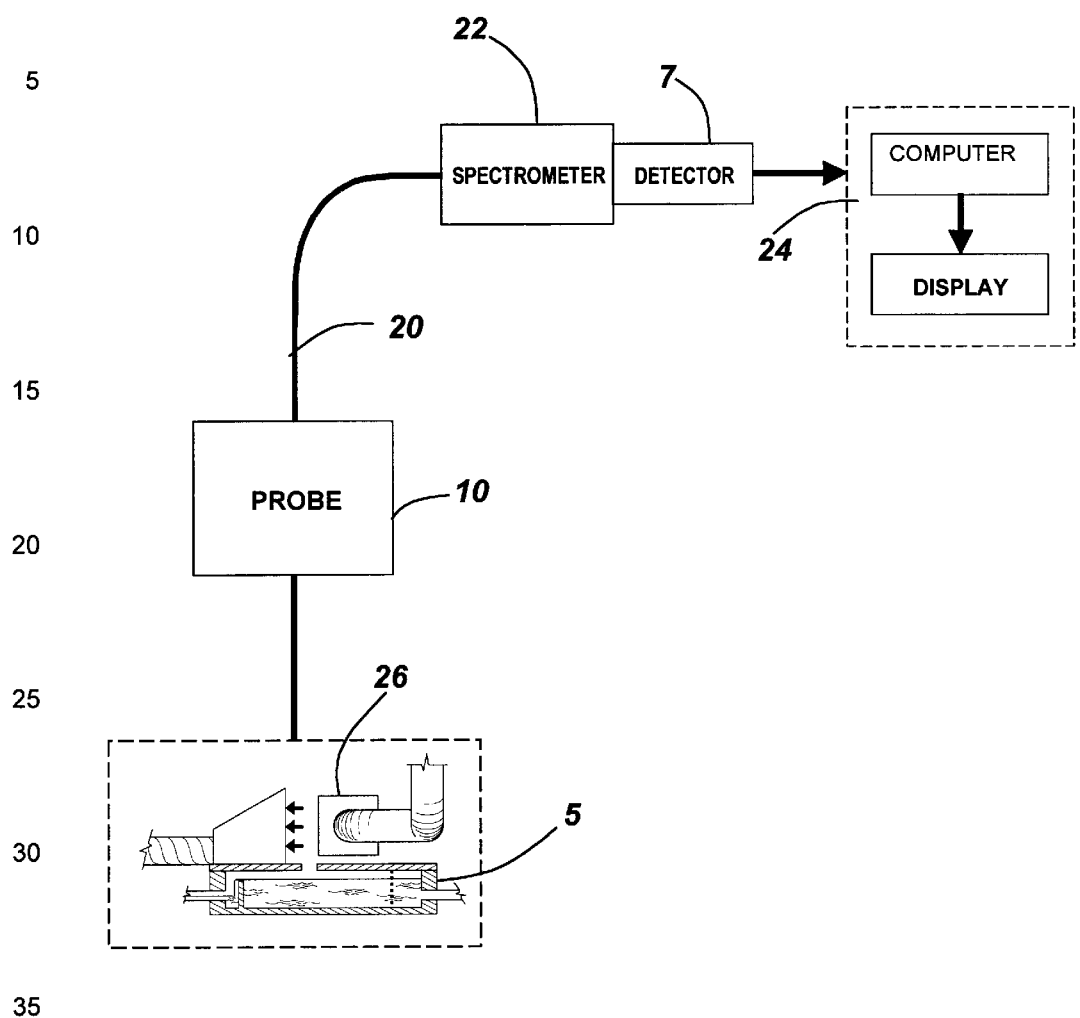
FIG. 1 is an overall block diagram of the apparatus.
Figure 2:
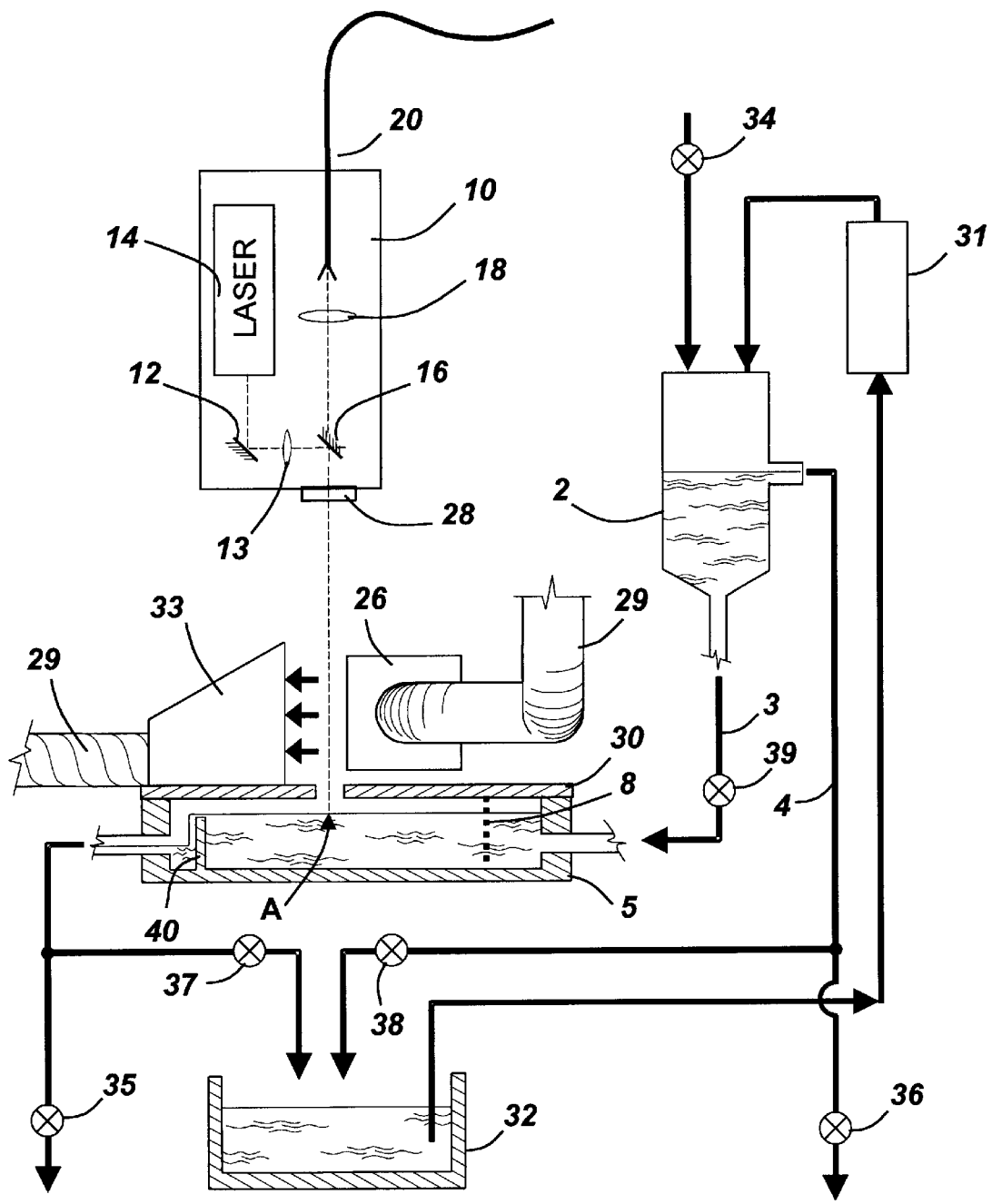
FIG. 2 shows a detailed set-up for the flow cell.

FIGS. 1 and 2 respectively show a block diagram and schematic diagram of the apparatus according to the present invention. The individual components shown in outline or designated by blocks in these figures are all well-known in the LIBS arts, and their specific construction and operation are not critical to the operation or best mode for carrying out the present invention. The probe 10 includes a first mirror 12 that reflects a laser pulse (generated by the laser source head 14) by ninety degrees to a focusing lens 13. The second (dichroic) mirror 16 reflects the laser pulse at ninety degrees to the surface of liquid point (A) located in the bath of the flow cell 5. Spectral response signals generated by plasma created at the liquid surface (A) by the application of the laser pulse to the liquid surface are focused by a second lens 18 at the entrance of fiber optic 20. The light is guided by fiber optic to the spectrometer 22, which will be described in more detail later. Detection signals generated by a photodiode array or a CCD camera or PMs (photomultipliers) of a detection portion 7 of the spectrometer are supplied to the computer control-processing unit 24 for processing and treatment of data, and for the evaluation of the data to determine the concentration of various elements within the liquid. A blower 26 is located just above the flow cell 5. It prevents the debris, particles, or drops of liquid (aerosols) generated by the laser pulse focused on the sample from reaching the quartz window 28 by blowing air perpendicular to the laser beam. It also clears aerosols formed by the laser pulse from the path of the laser beam, which enables laser pulses to reach the sample without being absorbed by these aerosols. It should be noted that, although air is usually the gas blown above the sample cell, in some cases it advantageous to blow another gas either because the air components (oxygen, nitrogen) have an adverse reaction with the liquid and modify its composition at the surface or for increasing the sensitivity of the technique (for example by using helium).

FIG. 2 shows a more detailed lateral view of the flow cell. As schematically illustrated in this figure, the reservoir 2 is fed by a flow of liquid coming from the pump 31 that allows circulation of liquid from a reservoir 32 or from the liquid stream of the process to be analyzed. The velocity of the liquid in the tube 3 is maintained constant by keeping the height of the liquid in the reservoir 2 at the level of the evacuation tube 4. When the feeding flow of the pump or the liquid stream exceeds the flow of the tube 3, the tube 4 will evacuate the extra flow. As a result, the heights of the liquid in the reservoir 2 and cell 5 are maintained substantially constant, which ensures a uniform flow through the cell 5 and a stable surface. The speed and surface position of the liquid can be controlled by the height of the reservoir 2 above the cell 5, the flow control valve 39, the height of the weir 40, and the cross-section area of the bath 5. The flow cell operates in two modes, depending on the feeding flow from the pump or the process; the closed mode (valves 34, 35 and 36 closed, valves 37 and 38 opened) is used to calibrate the system while the open mode (valves 34, 35 and 36 opened, 37 and 38 closed) is devoted to on-line measurement of the liquid stream to be analyzed. To promote steady controlled flow of the liquid and ensure that the probed surface is representative of the bulk or volume, which is in many cases an important feature, a mixing screen 8 is placed at the entrance of the bath. Although other mixing devices can be used, it was found that a simple screen made by perforated plate was quite appropriate for this purpose. Furthermore, the weir 40 and the mixer 8 permit ensuring a stable surface by breaking the wave generated by the laser pulse on the surface of the liquid, enabling the laser to sample a stable surface and improving the reproducibility and the accuracy of the measurement.

The liquid (for example water with a low concentration of calcium) enters the end of the 12 inch long, 2 inch deep and ¾ inch wide high density polyethylene sample cell (or bath) 5 via a flow control valve 39 and half inch diameter pipe 3, and the liquid is transformed into a uniform flow by means of a PVC mixing plate 8 perforated with ⅛ inch diameter holes on 7/32 inch staggered centers and a weir 40. Constant liquid depth is maintained at 1.75 inch by a constant feeding head, and a weir 40 at the outflow end of the cell. A flow rate of between 1 and 1.5 l/min thus produced is sufficient to prevent any bubbles (by sweeping the bubbles from the analyzed region of the liquid) generated by laser pulses from interfering with subsequent measurements performed at a 1 Hz pulse repetition rate. At this repetition rate and for the relatively small cross section of the cell, this flow is also sufficient for carrying away from the probed location the waves produced at the surface of the liquid by the laser interaction. A blower 26, such as the 26 CFM flatpak EBM Pabst model RL 90-18-00, positioned to blow air parallel and close to the liquid surface, deflects splashed or otherwise ejected liquid, thus substantially reducing contamination of a 2 inch diameter optical window 28 positioned about 12 inches above the liquid. Four inch ducting 29 is used to channel air to the blower, and, via a collection funnel 33, to remove it and ejected material, from the apparatus. An intake filter may be used to remove suspended particles from the air when such particles may trigger unwanted plasma emissions. A cell cover plate 30 with a ¾ inch hole centered on the laser beam near the center of the cell serves to shield the liquid from disturbance by the blower.

A suitable choice of laser with sufficient power to excite plasma with radiation characteristic of the composition of the liquid is the Big Sky Model CFR 400 Nd:YAG 400 mJ NIR laser, in combination with a 40 cm focal length focusing lens.

Optical emission from the plasma passes through a protective window 28 that is substantially collinear with the laser beam in this embodiment. The emission is separated from the path of the laser beam by a dichroic mirror and focused by a lens into optical fibers, whereby it is conveyed for analysis to an optical spectrometer. A 0.35 m Czerny-Turner spectrometer 22 with a 50 micron slit width and a 3600 grooves/mm grating may be used in conjunction with a gated intensified CCD camera 7, manufactured by Andor Technology. Alternatively, a photodiode array detector, or photomultipliers individually positioned to detect both emissions from elements present in the liquid and background radiation, may provide useful measurements. Selection of spectral peaks to be measured depends on the application. For the analysis of calcium in water, the ionic emission peak at 393.3 nm yields a linear calibration from 0 ppm to at least 500 ppm, using an acquisition delay of 1 microsecond and integration time of 5 microseconds. Continuum emission at a nearby wavelength with no spectral emission serves to normalize the measurement.

Figure 3:
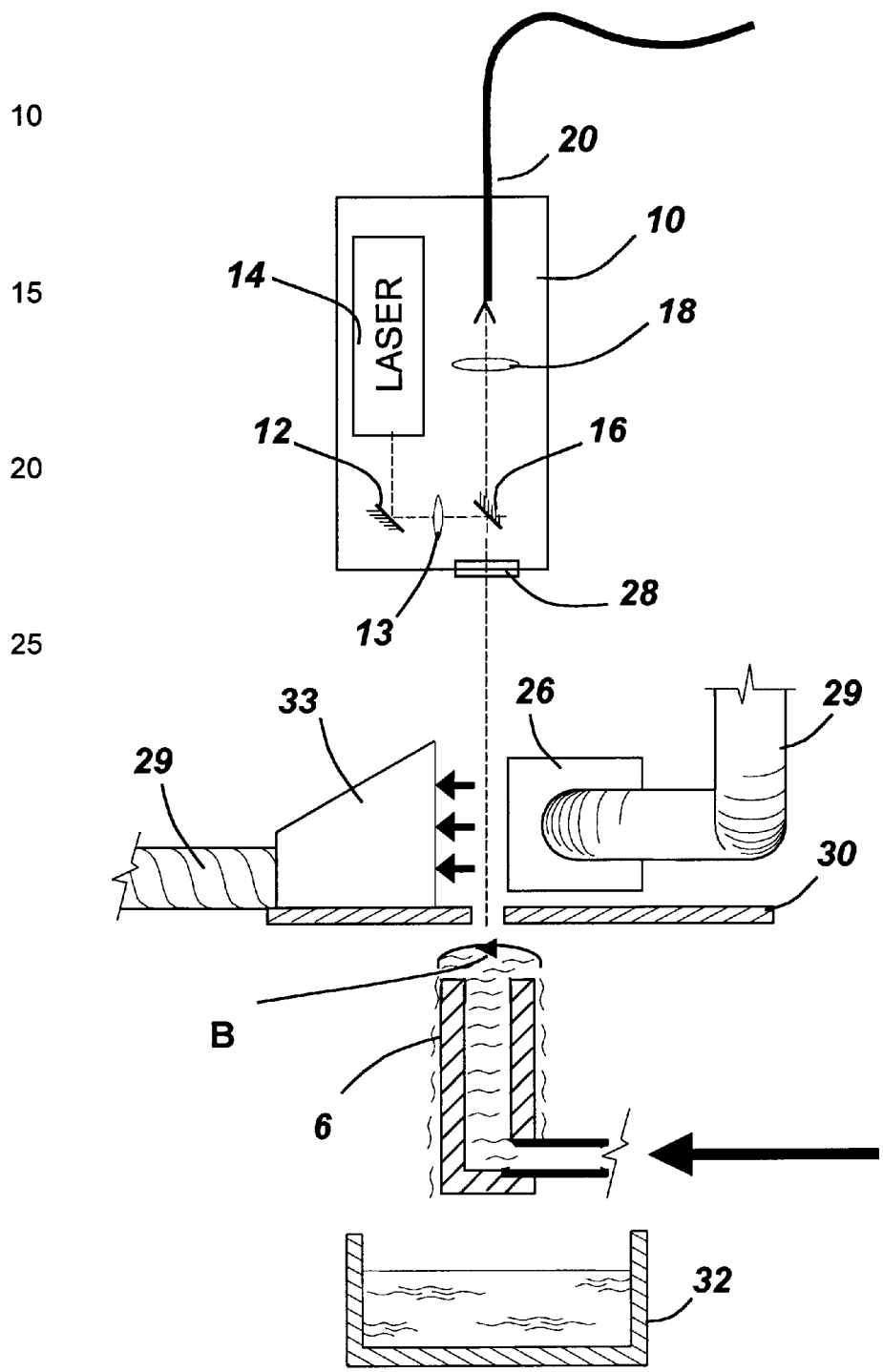
FIG. 3 shows another set-up for the flow cell.

FIG. 3 shows an alternate embodiment for the flow cell identified now with the numeral 6. In this configuration, the cell operates in similar manner as the one of FIG. 2 in a closed loop mode for calibration or an open mode for on-line measurements. In this embodiment, the laser samples the top of the fountain B and the waves and the bubbles generated by the laser pulse respectively on the surface and inside the liquid are broken and evacuated by the fallen flowing liquid. Similarly to the previous embodiment, the speed of evacuation can be controlled by the height of the reservoir 2 above the cell 6 and the size of this cell. Higher speed allows increasing the repetition rate of sampling by the laser and improving the reproducibility of the measurement. A cell cover plate 30 with a hole centered on the laser beam near the center of the cell serves to shield the liquid from disturbance by the blower 29.

An example of the spectrum obtained with the apparatus of FIG. 2 is shown in FIG. 4 (similar results would have been obtained with the configuration depicted in FIG. 3). The spectrum was obtained from an approximately 1 mm-diameter spot at the surface of water containing 50 ppm, of Ca by firing a single laser pulse shot of 200 mJ energy provided by a YAG laser at a wavelength of 1064 nm.

Table 1 shows a comparison of the measurement reproducibility obtained by focusing laser pulses on the surface of water with and without an air removal exhaust or blower. For quantitative analysis by laser-induced plasma spectroscopy, elements are monitored by the measurement of their spectral line intensities, which are proportional to the species concentrations. These line intensities are affected by several parameters. In particular, they are highly dependant on the amounts of vaporization and the degree of ionization, which can change as a function of laser wavelength, laser fluence, pulse-to-pulse variability, sample surface morphology, ambient gas pressure, and ambient gas species. When the bubbles created inside the liquid by the laser pulse burst at the surface, they change the angle of incidence between the laser beam at the liquid surface, which, in turn, can change the fluence of the laser, and the line intensity. Also aerosols created by the laser-liquid interaction absorb the laser beam and prevent partially the laser from reaching the surface of the sample. This absorption can change the reproducibility of the measurement by affecting the energy delivered to the sample. The results obtained in Table 1 show clearly the power of our invention, how the aerosols affect the results and how the use of the blower improves the accuracy of the measurements and make it possible to realize quantitative measurements.

TABLE 1

Comparison of the reproducibility of single shot laser measurements with and without air blowing and liquid motion

| Liquid | Blower | Net Amplitude Ca 393.3 nm | Std. Dev'n | SD/Amp % |
|---|---|---|---|---|
| Flowing | On | 9630 | 2631 | 27.3 |
| Flowing | Off | 5715 | 3314 | 58.0 |
| Stationary | Off | 5180 | 4037 | 77.9 |
| Stationary | On | 9883 | 3439 | 34.9 |

Table 1 also compares results obtained for the Ca 393.3 nm line with flowing and stationary water (moving and non-moving surfaces). Here again measurement accuracy is improved by our setup. Moreover this arrangement lends itself to the analysis of continuously flowing liquids. The calibration curve obtained with the system on water containing different Ca concentrations is shown in FIG. 4. One can appreciate the good linearity and reproducibility of the calibration curve obtained with this approach. Reproducibility for measurements based on 100 laser shots is better than 3%.

The embodiment described above uses a single laser pulse. It is known as it has been described by Sabsabi et al in U.S. Pat. No. 6,008,897 that the use of a second laser pulse could increase significantly sensitivity. A second laser pulse originating from the same laser unit or an independent laser whose beam is sent colinearly to the first beam by using suitable mixing optics could then be advantageously used in some cases with a moderate increase of complexity. It has also been found by Detalle et al as described in a Provisional U.S. patent application No. 60/251,183 and by St-Onge et al (Spectrochimica Acta B. 57, 121–136, 2002) that sending at the same time several pulses at different wavelengths (e.g. infrared and ultraviolet) increases sensitivity and this approach can also be used with the described system for analysis of liquid or molten materials.

This invention may be applied in a number of industrial processes. Aqueous acidic solution by-product from copper smelting containing dissolved metals requires costly treatment to precipitate metals prior to solution neutralization and disposal in an environmentally acceptable manner. Continuous analysis permits substantial cost savings through more accurate matching of reagent use to metal content. Other applications include in-process monitoring and control, as well as optimization of toxic effluent treatments in the electro-refining of copper. Aqueous effluent monitoring in mining and other industrial settings, as well as non-industrial effluent monitoring, are other uses for the present invention.

The present invention may also be applied in the pharmaceutical and other industries for both aqueous and non-aqueous liquids. In the pharmaceutical industry, for example, the invention may be used in various ways for the analysis of liquid products. One possibility is to exploit certain elements that are uniquely associated with active agents, as opposed to other components of the formulation, as indicators of concentration. Such elements may, for example, be phosphorus, sodium, sulfur, or sodium—all of which lend themselves to LIBS analysis which, using the present invention, may be performed in less than 1 minute. The alternative of off-line determination by liquid chromatography requires sample preparation and analysis that take one or more hours.

CONCLUSION

Thus, what has been described is an improved method and apparatus for in-situ transient spectroscopic analysis of liquid. While the present invention has been described with respect to what is presently considered to be the preferred embodiment, it is to be understood that the invention is not limited to the disclosed embodiment. To the contrary, the invention is intended to cover various modifications and equivalent arrangements included within the spirit and scope of the appended claims. Therefore, the scope of the following claims is to be accorded the broadest interpretation so as to encompass all such modifications and equivalents

What is claimed is:

1. A laser-induced plasma spectroscopy apparatus for the analysis of the composition of liquid and molten materials comprising:
    a laser emitting pulses at given repetition rate and along a given beam path;
    an optical means to direct the laser pulses to a location at a surface of the liquid to generate a plasma that emits elemental radiation that corresponds to at least one compositional element of the liquid;
    a probe structure, which detects the emitted elemental radiation along a detection path, said probe structure including an optical window, a spectrometer for analyzing the spectra of the emitted radiation, a detector to detect the light diffracted by the spectrometer, a data processor which determines a concentration of the predetermined element; and
    a flow cell assembly which establishes a substantially steady flow of the liquid past the said location at the surface of the liquid, the flowing liquid at this location being truly representative of the liquid bulk flown into the cell, said flow sufficient to prevent said pulses from perturbing said surface at said location, said cell assembly including a controller to control the liquid surface level and the flow speed.

2. An apparatus according to claim 1, wherein the controller comprises a pump to circulate the liquid in a closed loop.

3. An apparatus according to claim 1, wherein the controller includes a liquid vessel set above the probed liquid surface in the cell assembly and filled at a substantially constant level.

4. An apparatus according to claim 1 that includes further a liquid mixing means.

5. An apparatus according to claim 4 wherein the liquid mixing means is a perforated plate.

6. An apparatus according to claim 1, wherein the cell assembly is configured in such a way that the liquid overflows from all sides.

7. An apparatus according to claim 6 that includes further a liquid mixing means.

8. An apparatus according to claim 7 wherein the liquid mixing means is a perforated plate.

9. An apparatus according to claim 1, wherein said probe structure further comprises an optical structure configured so that the incident laser beam and the light collected from the plasma are substantially collinear.

10. An apparatus according to claim 1, further comprising fiber optic means to convey the elemental radiation emitted by the plasma to said spectrometer of said probe structure.

11. An apparatus according to claim 1, wherein the laser generates multiple pulses at the same wavelength separated by a short time interval, to produce and excite the plasma at the surface of the liquid.

12. An apparatus according to claim 1, wherein the laser generates multiple pulses at different wavelengths simultaneously or separated by a short time interval, to produce and excite the plasma at the surface of the liquid.

13. An apparatus according to claim 1, wherein said probe structure comprises an intensified photodiode array detector.

14. An apparatus according to claim 1, wherein said probe structure comprises a CCD camera.

15. An apparatus according to claim 1, wherein said probe structure comprises an intensified CCD camera.

16. An apparatus according to claim 1, wherein said probe structure comprises a plurality of photomultipliers positioned to detect both (i) emissions from the predetermined element and (ii) background radiation.

17. An apparatus according to claim 1, wherein the determination of concentration of a predetermined element is made by comparison with a predetermined calibration curve.

18. A method of laser-induced plasma spectroscopy analysis for liquid and molten materials, comprising the steps of:
    directing laser pulses at a given repetition rate and along a given beam path onto a location at the liquid surface to generate a plasma that emits elemental radiation that corresponds to at least one compositional element of the liquid;
    detecting the emitted elemental radiation along a detection path and analyzing its spectra with a spectrometer;
    processing the spectra to determine a concentration of the predetermined element; and
    establishing a substantially steady flow of liquid past the said location at the liquid surface, said flow sufficient to prevent said pulses from perturbing said surface at said location, the flowing liquid at this location being truly representative of the bulk of the liquid to analyze; and
    controlling the liquid surface level and the flow speed.

19. A method according to claim 18, wherein the step of controlling consists in establishing a substantially constant liquid level.

20. A method according to claim 19 wherein controlling is performed with a pump that circulates the liquid in a closed loop.

21. A method according to claim 19 wherein controlling is performed with a liquid vessel set above the probed liquid surface and maintained at a substantially constant level.

22. A method according to claim 18 wherein the step of establishing a flowing liquid at the said location substantially representative of the liquid bulk is obtained by mixing the liquid.

23. A method according to claim 18 wherein the liquid after passing through said location at the liquid surface flows in all directions before being discharged.

24. A method according to claim 18 wherein said laser beam path and detection path are substantially superimposed.

25. A method according to claim 18, further comprising the step of conveying the elemental radiation emitted by the plasma to the spectrometer in said detecting step using optical fiber optics.

26. A method according to claim 18 wherein the laser generates multiple pulses at the same wavelength separated by a short time interval to produce and excite the plasma at the surface of the liquid.

27. A method according to claim 18 wherein the laser generates multiple pulses at different wavelengths simultaneously or separated by a short time interval to produce and excite the plasma at the surface of the liquid.

28. A method according to claim 18, wherein said detecting step includes using a photodiode array detector.

29. A method according to claim 18, wherein said detecting step includes using a CCD camera.

30. A method according to claim 18, wherein said detecting step includes using an intensified CCD camera.

31. A method according to claim 18, wherein said detecting step includes using a plurality of photomultipliers positioned to detect both (i) emissions from the predetermined element and (ii) background radiation.

32. A method according to claim 18, wherein the step of processing the spectra to determine a concentration of the predetermined element is made by comparison with a predetermined calibration curve.

33. The apparatus of claim 1 wherein said flow is sufficient to prevent waves being induced at said location on said surface by said laser pulses.

34. The apparatus of claim 1 wherein said flow is sufficient to prevent bubbles induced in the liquid by said laser pulses from reaching said surface at said location.

35. The method of claim 18 wherein said flow is sufficient to prevent waves being induced at said location by said laser pulses.

36. The method of claim 18 wherein said flow is sufficient to prevent bubbles induced in the liquid by said laser pulses from reaching said surface at said location.

37. The apparatus of claim 1, which further comprises a gas flow generator to substantially prevent liquid drops, which are ejected from the liquid in response to the incident laser pulses, from accumulating on said optical window of said probe structure and along the laser beam path and the detection path.

38. The method of claim 18, which further comprises blowing gas above the liquid surface to substantially prevent liquid drops, which are ejected from the liquid in response to the incident laser pulses, from accumulating anywhere along the laser beam path and the detection path.

* * * * *